United States Patent
Piccardi et al.

(10) Patent No.: US 9,642,786 B2
(45) Date of Patent: May 9, 2017

(54) USE OF A COMBINATION OF AT LEAST ONE POLYUNSATURATED FATTY ACID AND AT LEAST ONE CAROTENOID, FOR IMPROVING THE QUALITY OF THE NAILS

(71) Applicant: NUTRICOS TECHNOLOGIES, Clichy (FR)

(72) Inventors: Nathalie Piccardi, Arceau (FR); Yann Mahe, Sainte Genevieve des Bois (FR); Carole Bru, Courbevoie (FR)

(73) Assignee: NUTRICOS TECHNOLOGIES, Clichy (FR)

( * ) Notice: Subject to any disclaimer, the term of this patent is extended or adjusted under 35 U.S.C. 154(b) by 0 days.

(21) Appl. No.: 14/432,398

(22) PCT Filed: Sep. 27, 2013

(86) PCT No.: PCT/IB2013/058931
§ 371 (c)(1),
(2) Date: Mar. 30, 2015

(87) PCT Pub. No.: WO2014/049562
PCT Pub. Date: Apr. 3, 2014

(65) Prior Publication Data
US 2015/0250691 A1    Sep. 10, 2015

(30) Foreign Application Priority Data
Sep. 28, 2012   (FR) ..................... 12 59217

(51) Int. Cl.
*A61K 8/36* (2006.01)
*A61K 8/31* (2006.01)
*A61Q 3/00* (2006.01)
*A61K 8/92* (2006.01)
*A23L 5/44* (2016.01)
*A23L 33/105* (2016.01)
*A23L 33/115* (2016.01)
*A23L 33/12* (2016.01)

(52) U.S. Cl.
CPC ............... *A61K 8/361* (2013.01); *A23L 5/44* (2016.08); *A23L 33/105* (2016.08); *A23L 33/115* (2016.08); *A23L 33/12* (2016.08); *A61K 8/31* (2013.01); *A61K 8/922* (2013.01); *A61K 8/925* (2013.01); *A61Q 3/00* (2013.01); *A23V 2002/00* (2013.01); *A61K 2800/884* (2013.01); *A61K 2800/92* (2013.01)

(58) Field of Classification Search
None
See application file for complete search history.

(56) References Cited

U.S. PATENT DOCUMENTS

2013/0004444 A1   1/2013   Baudouin et al.
2015/0030550 A1   1/2015   Baudouin et al.

FOREIGN PATENT DOCUMENTS

| AU | 30756/89 A | 8/1989 | |
| EP | 0 330 583 A2 | 8/1989 | |
| FR | 2 953 722 A1 | 6/2011 | |
| GB | WO 2009115769 A1 * | 9/2009 | ............ A61K 8/0216 |
| WO | 2006/104730 A1 | 10/2006 | |
| WO | WO 2006104730 A1 * | 10/2006 | ............ A23L 1/3008 |
| WO | 2009/115769 A1 | 9/2009 | |

OTHER PUBLICATIONS

Mintel "Skin, Hair & Nails Suppl" Nov. 2008 Database A.N. 1011830.*
"Skin, Hair & Nails Supplement," Mintel, Database accession No. 1011830, 2008.
Jul. 2, 2013 Written Opinion issued in French Application No. 1259217.
Jun. 20, 2014 International Search Report issued in International Application No. PCT/IB2013/058931.
Jun. 20, 2014 Written Opinion of the International Searching Authority issued in International Application No. PCT/IB2013/058931.

* cited by examiner

*Primary Examiner* — Heidi Reese
(74) *Attorney, Agent, or Firm* — Oliff PLC

(57) ABSTRACT

The invention relates to the oral cosmetic use of a combination of active agents comprising at least one polyunsaturated fatty acid and at least one carotenoid, for improving the quality of the nails. More particularly, the present invention relates to the oral cosmetic use of such a combination for improving the solidity of the nails and for reducing and/or preventing their splitting.

11 Claims, No Drawings

USE OF A COMBINATION OF AT LEAST ONE POLYUNSATURATED FATTY ACID AND AT LEAST ONE CAROTENOID, FOR IMPROVING THE QUALITY OF THE NAILS

The present invention relates to the field of cosmetic products and food supplements intended for improving the quality of the nails.

More particularly, the present invention proposes the use of a novel combination of active agents for reducing and/or preventing aesthetic defects, and/or for improving the solidity or hardness of the nails. The invention is also directed towards the use of a combination of active agents in accordance with the invention for reducing and/or preventing splitting of the nails.

The present invention also relates to a cosmetic process for improving the quality of the nails, in an individual in need thereof, characterized in that it comprises at least the oral administration, to the said individual, of a combination of active agents or of a composition in accordance with the invention.

A nail or ungual plaque is a flexible, translucent, sleek horny blade which forms a surface excrescence of the skin, consisting of keratinocytes and a very dense and homogeneous keratin matrix. This matrix keeps the cells welded together and gives the nail its strength, hardness, solidity and flexibility. The nail is enveloped by an epidermal sheath, or matrix.

From a morphological viewpoint, a nail consists of a dorsal part, an intermediate part, a ventral part, a proximal matrix, an intermediate matrix, a lunula and the nail bed. 80% of the thickness of a nail is produced by the proximal matrix, and 20% of its thickness is produced by the intermediate matrix and the nail bed. The dorsal part consists of hard keratin, the intermediate part is the thickest and is formed of moderately hard keratin, and the ventral part consists of soft keratin.

As regards its chemical constitution, a nail contains water, lipids, mucopolysaccharides and minerals, such as sodium, potassium, iron, calcium, zinc or silicon.

The hardness and flexibility of nails depend especially on the orientation of the keratin fibres, the arrangement of the keratinocytes and their cohesion and chemical constitution, in particular the content of water, lipids and phospholipids.

Many factors may impair the chemical constitution of the nails, and as a result their hardness or shape.

Among the extrinsic factors that are liable to affect the nails, mention may be made of exposure to sunlight, exposure to temperature and/or humidity variations, and exposure to pollutants or to cigarette smoke. Among the intrinsic factors affecting the nails, mention may be made of stress, fatigue, hormonal changes, dehydration, a metabolic deficit, ageing or certain pathologies.

These various factors are liable to make the nails fragile or brittle, affect their shape, make them split, and thus greatly reduce their aesthetic appeal.

At the present time, the main solutions proposed in the field of nail quality are based on the use of nail varnishes, of moisturizing active agents in handcare products, or of chemical reinforcement of the nail. The latter solution is based on the use of nail-hardening agents, such as formaldehyde at 1-2%, which generate crossbonds in the keratin. However, frequent use of these products may give rise to too many crossbonds, paradoxically promoting embrittlement of the nails.

Temporary implants, such as false nails, have also been proposed in the field of nail quality, but the main aim thereof is to hide the poor quality of the nails rather than to prevent and/or restore their quality.

From a cosmetic viewpoint, there is thus a need to be able to reduce or prevent the various aesthetic impairments that may affect the nails, irrespective of the origin of these impairments.

There is also a need for novel active agents or for a combination of active agents that can exert efficient and beneficial action on the quality of the nails, and in particular on their hardness, their solidity, their resistance to impacts or to external attacking factors, their resistance to splitting, their smooth appearance, their sheen and consequently their general aesthetic appearance.

There is more particularly a need for novel active agents or a combination of active agents that are capable of exerting efficient action on the solidity of the nails and of reducing and/or preventing their splitting.

The object of the present invention is to satisfy these needs.

Thus, according to a first aspect, the present invention relates to the oral cosmetic use of a combination of active agents comprising at least one polyunsaturated fatty acid and at least one carotenoid, for improving the quality of the nails.

Lycopene is already described in the prior art either as an antioxidant or as an antitumour agent (Kelkel et al, Free Radic. Res. 2011 August; 45(8):925-40).

It is also used in compositions with tanning activity for its role in melanin synthesis (WO 97/47278), in compositions intended for treating the hair and/or acne for its activity on 5α-reductases (JP-2940964) or as a free-radical scavenger.

To the inventors' knowledge, it has never been proposed or suggested hitherto that the oral administration, to an individual in need thereof, of a combination of polyunsaturated fatty acid and of at least lycopene, as active agents, could prove to be particularly effective for improving the quality of the nails.

More particularly, the oral administration of a cosmetic combination of active agents in accordance with the invention makes it possible to make the nails more solid, and thus to reduce and/or prevent the nails from breaking and/or splitting.

More particularly, the oral administration of a cosmetic combination of active agents in accordance with the invention makes it possible to reduce and/or prevent lamellar and/or transverse separations of the nails, and especially their splitting.

More particularly, the oral administration of a cosmetic combination of active agents in accordance with the invention makes it possible to improve the hardness of the nails, and thus to reduce and/or prevent soft or overly flexible nails.

More particularly, the oral administration of a cosmetic combination of active agents in accordance with the invention makes it possible to improve the general aesthetic appearance of the nails, and especially to reduce and/or prevent striated and/or damaged nails.

More particularly, the oral administration of a cosmetic combination of active agents in accordance with the invention makes it possible to improve the sheen and/or transparency of the nails.

Furthermore, due to the improvement in the quality of the nails associated with the oral administration of a cosmetic combination of active agents in accordance with the invention, such an administration also advantageously makes it possible to have longer nails. This also makes it possible to facilitate the wear property of nail varnishes.

More particularly, the oral administration of a cosmetic combination of active agents in accordance with the invention makes it possible to improve the aesthetic appearance of the cuticle of the nails.

The administration of a combination of active agents in accordance with the invention also enables the nails more quickly to regain a sleek and shiny appearance after the removal of false nails and/or to protect the nails in the event of the application of false nails.

Thus, the administration of a combination of active agents in accordance with the invention makes it possible to reinforce the quality of the nails. In particular, it enables the nails to become harder, less brittle, more resistant to impacts, less prone to splitting and to have a sleek, homogeneous and translucent appearance, and also an improved general aesthetic appearance, especially with less damaged and less striated, or even unstriated, nails.

According to one embodiment, the combination of active agents in accordance with the invention may be used in a cosmetic composition that is suitable for oral administration.

A cosmetic composition in accordance with the invention gives the same advantages as those afforded by the combination of active agents in accordance with the invention, as indicated previously.

According to yet another of its aspects, the subject of the present invention is a cosmetic treatment process for improving the quality of the nails, in an individual in need thereof, characterized in that it comprises at least the oral administration, to the said individual, of a combination of active agents or of a composition in accordance with the invention.

The use of a combination of active agents in accordance with the invention is necessarily performed in an effective amount, i.e. an amount that enables the active agents to manifest their properties with regard to the improvement to be afforded to the quality of the nails.

For the purposes of the present invention, the term "prevent" means reducing to a lesser extent the risk or probability of manifestation of a given phenomenon, i.e. in the present invention impairment of the quality or aesthetic appearance of the nails.

According to yet another of its aspects, the present invention relates to a combination of active agents comprising at least one polyunsaturated fatty acid, lycopene and vitamin C. Preferably, a combination of active agents in accordance with the invention also comprises vitamin E.

According to yet another of its aspects, the present invention relates to a cosmetic composition that is suitable for oral administration, comprising at least fish oil, lycopene and vitamin C. Preferably, a cosmetic composition in accordance with the invention also comprises vitamin E.

According to yet another of its aspects, the present invention relates to a cosmetic composition that is suitable for oral administration, comprising at least blackcurrant seed oil, lycopene and vitamin C. Preferably, a cosmetic composition in accordance with the invention also comprises vitamin E.

According to yet another of its aspects, the present invention relates to a cosmetic composition that is suitable for oral administration, comprising at least blackcurrant seed oil, fish oil, lycopene and vitamin C. Preferably, a cosmetic composition in accordance with the invention also comprises vitamin E.

For the purposes of the present invention, the term "splitting of the nail" means both lamellar splitting (or onychoschizia) and longitudinal separation of the nail (or onychorrhexis). Preferably, for the purposes of the present invention, the term "splitting of the nail" means lamellar splitting (or onychoschizia).

The term "onychoschizia" means the deterioration of the intracellular adhesion factors of the nails, which is characterized by lamellar cracking of the end of the nail and also of its distal portion. [Van de Kerkhof et al., 2005; Kechijian, 1985].

The term "onychorrhexis" means a state characterized by vertical cracking or edges on the nails.

According to yet another of its aspects, the present invention relates to a packaging kit or assembly comprising:

(i) a combination of active agents in accordance with the invention intended for oral administration, and (ii) an antifungal agent which is intended for topical application, the combination of active agents and the antifungal agent (i) and (ii) being intended to be administered independently of each other, separately, simultaneously or consecutively over time, the antifungal agent (ii) advantageously being administered before the combination of active agents (i).

According to yet another of its aspects, the present invention relates to a packaging kit or assembly comprising:

(i) a combination of active agents in accordance with the invention intended for oral administration, and (ii) a moisturizer and/or a hardener intended for topical application, the combination of active agents (i) and the moisturizer and/or hardener (ii) being intended to be administered independently of each other, separately, simultaneously or consecutively over time.

The present invention also describes a packaging kit or assembly comprising:

(i) a combination of active agents in accordance with the invention intended for oral administration, and (ii) a nail varnish intended for topical application to at least one nail.

The present invention also describes a packaging kit or assembly comprising:

(i) a combination of active agents in accordance with the invention intended for oral administration, and (ii) at least one false nail intended to be applied topically onto at least one nail.

Polyunsaturated Fatty Acids

For the purposes of the present invention, the term "polyunsaturated fatty acid" means a fatty acid comprising at least two double bonds. Such fatty acids are more particularly long-chain fatty acids, i.e. containing at least 14 carbon atoms.

The polyunsaturated fatty acids may be in acid form, in triglyceride form or in the form of methyl or ethyl esters.

The polyunsaturated fatty acids especially comprise ω-3 fatty acids, ω-6 fatty acids and ω-9 fatty acids, characterized by the position of the unsaturation that is closest to the end methyl group, and mixtures thereof.

Unsaturated fatty acids comprising from 18 to 22 carbon atoms are most particularly suitable for use in the invention, in particular polyunsaturated fatty acids, especially ω-3, ω-6 and ω-9 fatty acids.

Among the polyunsaturated fatty acids of the ω-6 series, mention may be made in particular of linoleic acid containing 18 carbon atoms and two unsaturations (18:2 ω-6), γ-linolenic acid containing 18 carbon atoms and three unsaturations or GLA (18:3 ω-6), di-homo-γ-linolenic acid containing 20 carbon atoms and three unsaturations (20:3

ω-6), arachidonic acid, 5, 8, 11, 14 eicosatetraenoic acid (20:4, ω-6) and docosatetraenoic acid (22:4, ω-6).

The polyunsaturated fatty acids of the ω-3 series may be chosen especially from α-linolenic acid or ALA (18:3 ω-3), stearidonic acid or SDA (18:4 ω-3), 5,8,11,14,17-eicosapentaenoic acid or EPA (20:5 ω-3), and 4,7,10,13,16,19-docosahexaenoic acid or DHA (22:6 ω-3), docosapentaenoic acid or DPA (22:5 ω-3) and n-butyl-5,11,14-eicosatrienonic acid.

The polyunsaturated fatty acids of the ω-9 series may be chosen especially from oleic acid (18:1, ω-9) and erucic acid (22:1, ω-9).

α-Linolenic acid, linoleic acid, γ-linolenic acid, stearidonic acid, eicosapentaenoic acid, docosahexaenoic acid, oleic acid, mixtures thereof or extracts comprising them are most particularly suitable for use in the invention.

According to one variant of the invention, the polyunsaturated fatty acid(s) under consideration are used in an isolated form, i.e. after extraction from their sources of origin.

Isolated polyunsaturated acids in accordance with the invention may especially be those sold by the companies Polaris and Bioriginal, under the names Omegavie 1812 TG and Blackcurrant Oil Refined 806000.

The polyunsaturated fatty acid content in a composition in accordance with the invention may range from 1% to 80% by weight, especially from 5% to 70% by weight, in particular from 10% to 60% by weight and preferentially from 20% to 40% by weight relative to the total weight of the composition.

The sources of polyunsaturated fatty acid may be chosen from plant oils, for instance evening-primrose oil, borage oil, blackcurrant seed oil, Ecchium oil and hemp oil, and extracts of the microalga *Schizochytrium* sp, preferably blackcurrant seed oil.

Plant oils from walnut, hazelnut, almond (*Juglans regia*), coriander, soybean (*Glycina max*), rapeseed (*Brassica naptus*), chia, linseed and fish oils, for example, are rich in polyunsaturated fatty acids of the ω-3 series.

ω-3 polyunsaturated fatty acids may also be found in zooplankton, shellfish/molluscs and fish. Fish oils are the main industrial source of EPA and DHA. Microalgal biomass may also constitute a raw material for the extraction of ω-3 unsaturated fatty acids.

Thus, a polyunsaturated fatty acid may be used in a combination of active agents in accordance with the invention in the form of at least one oil chosen from evening primrose oil, borage oil, blackcurrant seed oil, walnut oil, soybean oil, fish oil, sunflower oil, wheatgerm oil, hemp oil, fenugreek oil, Ecchium oil, argan oil, rice bran oil, sesame oil, almond oil, hazelnut oil, chia oil, linseed oil, olive oil, avocado oil, safflower oil, camelina oil, raspberry seed oil, cranberry seed oil, blueberry seed oil, *Rubus chamaemorus* Linné oil, sea buckthorn oil, cumin oil, kiwi seed oil, coriander oil and/or an extract of microalgae (for example *Schizochytrium sp*) and/or extracts of zooplankton and/or extracts of shellfish/molluscs.

The oil is preferably a blackcurrant seed oil and/or a fish oil, preferentially a blackcurrant seed oil and a fish oil.

Oils in accordance with the invention may especially be those sold by the companies Polaris and Bioriginal, under the names Omegavie 1812 TG and Blackcurrant Oil Refined 806000.

A composition according to the invention, as developed hereinbelow, may comprise these oils and/or extracts and/or biomass in a content ranging from 20% to 95% by weight, especially from 30% to 95% by weight and preferably from 50% to 80% by weight relative to the total weight of the composition.

A composition in accordance with the invention, as developed hereinbelow, may comprise these oils and/or extracts and/or biomass in an adjusted concentration such that they are administered in a content ranging from 100 mg to 5000 mg/day and especially from 200 mg to 2000 mg/day.

Thus, according to a preferred embodiment, a combination of active agents in accordance with the invention comprises at least one oil chosen from a blackcurrant seed oil and/or a fish oil.

According to a more preferred embodiment, a combination of active agents in accordance with the invention comprises a blackcurrant seed oil and a fish oil.

Carotenoids

A combination according to the invention comprises at least one carotenoid.

In the context of present invention, the term "carotenoid" is intended to mean both a carotenoid with provitamin A activity and a carotenoid with no provitamin A activity.

Needless to say, according to the invention, the carotenoid may be a mixture of carotenoids with provitamin A activity and of carotenoids with no provitamin A activity. This mixture may be in any proportion.

According to the invention, the carotenoid with provitamin A activity may be a mixture of carotenoids with provitamin A activity. This mixture may be in any proportion. Among the carotenoids with provitamin A activity, examples that may be mentioned include β-carotene or α-carotene, preferably β-carotene.

According to the invention, the carotenoid with no provitamin A activity may be a mixture of carotenoids with no provitamin A activity. This mixture may be in any proportion. Among the carotenoids with no provitamin A activity, examples that may be mentioned include zeaxanthin, cryptoxanthin, lutein or lycopene.

More particularly, the carotenoid used in the context of the present invention is lycopene.

In other words, the carotenoid present in the oral composition of the present invention comprises, or even consists of, lycopene.

A carotenoid in accordance with the invention may also be astaxanthin.

The carotenoid used according to the invention may be of natural or synthetic origin. The term "natural origin" is intended to mean the carotenoid in pure form or in solution irrespective of its concentration in the said solution, obtained from a natural element, such as a plant extract. For example, when the carotenoid is lycopene, a tomato extract may more particularly be used.

Thus, according to a preferred embodiment of the invention, the carotenoid used in a combination according to the invention is lycopene, preferably in a lycopene-rich tomato extract.

The term "synthetic origin" is intended to mean lycopene, in pure form or in solution irrespective of its concentration in the said solution, obtained via chemical synthesis. The lycopene which may be used in the context of the present invention may be in cis or trans chemical form.

When the carotenoid is of natural origin, it may be obtained from plant material derived from the whole plant cultivated in vivo or derived from in vitro culture.

The term "cultivated in vivo" is intended to mean any culture of standard type, i.e. in soil in the open air or in a greenhouse, or alternatively out of the soil.

The term "in vitro culture" is intended to mean all the techniques known to those skilled in the art for artificially obtaining a plant or a plant part. The selection pressure imposed by the physicochemical conditions during the growth of plant cells in vitro makes it possible to obtain a standardized plant material that is available throughout the year, in contrast with plants cultivated in vivo.

Preferentially, according to the invention, a plant derived from in vivo culture is used. Any extraction method known to those skilled in the art may be used to prepare the carotenoid used according to the invention.

Very preferentially in the case of lycopene, a lycopene-rich tomato extract is used.

Lycopene is also present in melon, guava and grapefruit.

The lycopene may be in alcoholic solution, in particular ethanolic solution. The carotenoid may also be in lipidic or lipoalcoholic solution.

By way of example, according to the invention, a lycopene-rich tomato extract, prepared by the company Lycored, sold under the name Lyc-O-Mato®, consisting of an oleoresin extract containing, for example, from 6% to 10% of pure lycopene, may be used.

The lycopene may be in an aqueous suspension. For this, it is possible to use forms that are water-dispersible, under cold or hot conditions, as sold by the company Lycored under the name Lyc-o-Mato CWD.

Any other more complex lycopene-based ingredient may also be used for implementing the invention.

Thus, a "more complex ingredient" is intended to mean, for example, a primary composition comprising lycopene and a whey protein. This primary composition is especially described in document WO 01/91588. This primary composition is also known as lactolycopene. It is this ingredient which is used in the food supplement of Example 1. It has the advantage of increasing the bioavailability of the lycopene and/or of being easy to formulate in food supplements (sachet, gel capsule, tablet, coated tablet, soft capsule, etc., forms).

The lacto lycopene may in particular be sold by the company Indena.

The amount of extract that may be used according to the invention obviously depends on the desired effect, and may thus vary within a wide range.

The carotenoid content in a composition in accordance with the invention may range from 0.01% to 6% by weight, especially from 0.02% to 4% by weight and in particular from 0.05% to 2% by weight relative to the total weight of the composition.

Thus, a combination of active agents in accordance with the invention advantageously comprises at least one oil comprising polyunsaturated fatty acids and isolated lycopene and/or a lycopene-rich extract.

According to a preferred embodiment, a combination of active agents in accordance with the invention comprises fish oil and/or blackcurrant seed oil and a tomato extract.

According to a more preferred embodiment, a combination of active agents in accordance with the invention comprises fish oil, blackcurrant seed oil and a tomato extract.

According to the present invention, the polyunsaturated fatty acid and the carotenoid, preferably lycopene, are used in a polyunsaturated fatty acid/carotenoid ratio of between 55/6 and 500/0.5, preferably between 120/8 and 400/0.5 and even more preferably between 19/1 and 300/0.5.

Additional Active Agent(s)

A combination of active agents in accordance with the invention may also comprise one or more additional cosmetic active agents.

Advantageously, such an additional cosmetic active agent may be intended to reinforce the desired cosmetic effect as described previously.

As additional active agents that may be used, mention may be made of:
  vitamins, such as vitamin A, $B_5$, $B_6$, $B_8$, C, E or PP (vitamin $B_3$ or niacin),
  antioxidants, such as curcuminoids; carotenoids, especially chosen from β-carotene, astaxanthin, zeaxanthin and lutein or compounds containing the same, such as wolfberry or lactowolfberry; polyphenol compounds, flavonoids such as catechins; proanthocyanidins, anthocyanins, PCOs (procyannidol oligomers); ubiquinones; coffee extracts containing polyphenols and/or diterpenes; chicory extracts; *Ginkgo biloba* extracts; grape extracts rich in proanthocyanidins; pimento extracts; soybean extracts; cocoa or coconut milk; pomegranate; Emblica,
  minerals such as zinc, calcium, magnesium, copper, iron, iodine, manganese, selenium and chromium (III),
  sugars,
  amino acids, especially sulfur amino acids such as glutathione precursors, selenium amino acids and citrulline,
  phytosterols,
  le resveratrol,
  hesperidin and neohesperidin,
  orthosilicic acid and monomethylsilanetriol,
  arterial pressure modulators, and
  mixtures thereof.

Preferably, a combination of active agents in accordance with the invention comprises, besides at least one polyunsaturated fatty acid and lycopene, vitamin C and/or vitamin E, preferentially vitamin C and vitamin E.

A combination of the invention may contain, besides the additional active agents indicated previously, one or more divalent mineral cations in various forms.

A divalent mineral cation may thus be in the form of an anhydrous or hydrated mineral or organic salt or a chelated complex. The salts may be, for example, carbonates, bicarbonates, sulfates, glycerophosphates, chlorides, nitrates, acetates, hydroxides, oxides, α-hydroxy acid salts (citrates, tartrates, lactates, malates) or fruit acid salts, or alternatively amino acid salts (aspartate, arginate, fumarate) or fatty acid salts (palmitate, oleate, caseinate, behenate).

A divalent mineral cation may be chosen from manganese, copper and/or zinc or from alkaline-earth metals. As alkaline-earth metals that may be used in the invention, mention may be made of barium, calcium, magnesium, strontium and/or beryllium.

Advantageously, a divalent mineral cation, and especially an alkaline-earth metal, is used in the present invention in salt form. In particular, the salt may be chosen from nitrate, citrate, chloride, gluconate, sulfate, lactate and/or acetate salts.

A divalent mineral cation may also be used in the form of a chelated complex, especially chelated to crystalline or ionized proteins.

A divalent mineral cation may also be in a specific form stored by a microorganism, for example such as a yeast, like selenium yeasts.

According to another embodiment, a combination of the invention may contain non-photosynthetic, non-fructifying filamentous bacteria or bacterial extracts derived from non-photosynthetic, non-fructifying filamentous bacteria as defined according to the classification in Bergey's Manual of Systemic Bacteriology, volume 3, section 23, 9th edition, 1989.

Mention may be made in particular of bacteria belonging to the order of *Beggiatoales*, and especially bacteria belonging to the genus *Beggiatoa*. Mention may moreover be made of bacteria belonging to the genus *Vitreoscilla*, which is similar to the genus *Beggiatoa*. Among the bacteria that may be used, mention may be made, for example, of *Vitreoscilla beggiatoides* (ATCC 43181) and *Beggiatoa alba* (ATCC33555), and preferentially the use of the extract of *Vitreoscilla filiformis*, in particular with the strain ATCC 15551, metabolites thereof and fractions thereof will be used.

According to one embodiment, a combination of active agents in accordance with the invention may comprise additional hydrophilic active agents. Hydrophilic active agents that may be used include proteins or protein hydrolysates, amino acids, polyols, especially of $C_2$ to $C_{10}$, for instance glycerol, sorbitol, butylene glycol or polyethylene glycol, urea, allantoin, sugars and sugar derivatives, water-soluble vitamins, starch, and bacterial or plant extracts, for instance those from Aloe vera.

According to one embodiment, a combination of active agents in accordance with the invention may also comprise a lipophilic active agent. Lipophilic active agents that may be used include retinol (vitamin A) and derivatives thereof, ceramides and essential oils.

As indicated previously, a combination of active agents in accordance with the invention may comprise, in addition to at least one polyunsaturated fatty acid and lycopene, at least one arterial pressure modulator.

Arterial pressure biological modulators are known to those skilled in the art.

An arterial pressure modulator in accordance with the invention may be chosen from vitamin D, taurine, cysteine, arginine, citrulline, glutamate, tryptophan, leucine, a tripeptide chosen from Val-Pro-Pro (VPP) and isoleucine-proline-proline (IPP), adenosine, flavonoids from berries, onions, pomegranate, red wine, grapes (including the seeds), tea, cocoa and dark chocolate, coenzyme Q10 (CoQ), acetyl-L-carnitine, α-lipoic acid, soybean proteins, spirulina; a microorganism such as *Lactobacillus helveticus*, *Bifidobacterium longum*, *Lactobacillus acidophilus*, *L. casei*, *L. acidophilus*, *Saccharomyces cerevisiae*, *Streptococcus thermophilus*; prebiotic agents, chosen especially from oligosaccharides produced from glucose, galactose, xylose, maltose, sucrose, lactose, starch, xylan, hemicellulose and inulin; glutathione, soybean isoflavones (genistin, genistein, daidzin, daidzein, glycitin, glycitein, estradiol, estrone), soybean lecithin and a tomato extract, as sold under the trade name Fruitflow™, or mixtures thereof.

More particularly, the oligosaccharide comprises at least one fructo-oligosaccharide.

More particularly, a prebiotic that is suitable for use in the invention may comprise a mixture of fructo-oligosaccharide and of inulin.

Such an arterial pressure modulator may be present in a combination of active agents in accordance with the invention in a content of between 0.1% and 50% by weight, preferably between 1% and 40% by weight and preferentially between 2% and 30% by weight relative to the total weight of the combination.

According to a particular embodiment, a composition of the invention may also comprise at least one probiotic microorganism, a prebiotic agent or a mixture of probiotic microorganisms and a mixture of prebiotic agents.

Specific examples of probiotic microorganisms that are suitable for use in the invention are *Bifidobacterium adolescentis*, *Bifidobacterium animalis*, *Bifidobacterium bifidum*, *Bifidobacterium breve*, *Bifidobacterium lactis*, *Bifidobacterium longum*, *Bifidobacterium infantis*, *Bifidobacterium pseudocatenulatum*, *Lactobacillus acidophilus* (LC1, NCFB 1748); *Lactobacillus amylovorus*, *Lactobacillus casei* (Shirota), *Lactobacillus rhamnosus* (strain GG), *Lactobacillus brevis*, *Lactobacillus crispatus*, *Lactobacillus delbruckii* (subsp. *bulgaricus*, *lactis*), *Lactobacillus fermentum*, *Lactobacillus helveticus*, *Lactobacillus gallinarum*, *Lactobacillus gasseri*, *Lactobacillus johnsonii*, *Lactobacillus paracasei*, *Lactobacillus plantarum*, *Lactobacillus reuteri*, *Lactobacillus rhamnosus*, *Lactobacillus salivarius*, *Lactobacillus alimentarius*, *Lactobacillus curvatus*, *Lactobacillus casei* subsp. *casei*, *Lactobacillus sake*, *Lactococcus lactis*, *Enterococcus faecalis* or *faecium*, *Lactococcus lactis* subsp. *lactis* or *cremoris*, *Leuconostoc mesenteroides* subsp. *dextranicum*, *Pediococcus acidilactici*, *Sporolactobacillus inulinus*, *Streptococcus salvarius* subsp. *thermophilus*, *Streptococcus thermophilus*, *Staphylococcus carnosus*, *Staphylococcus xylosus*, *Saccharomyces* (*cerevisiae* or *boulardii*), *Bacillus* (*cereus* var. *toyo* or *subtilis*), *Bacillus coagulans*, *Bacillus licheniformis*, *Escherichia coli* strain nissle, *Propionibacterium freudenreichii*, and mixtures thereof.

The microorganisms may be formulated in the form of powders, i.e. in a dry form, or in the form of suspensions or solutions.

More particularly, they may be probiotic microorganisms chosen from microorganisms of the genus *Lactobacillus* sp. and/or *Bifidobacterium* sp., a fraction thereof and/or a metabolite thereof. As illustrations of these microorganisms, mention may be made more particularly of *Lactobacillus johnsonii*, *Lactobacillus reuteri*, *Lactobacillus rhamnosus*, *Lactobacillus paracasei*, *Lactobacillus casei*, *Bifidobacterium bifidum*, *Bifidobacterium breve*, *Bifidobacterium longum*, *Bifidobacterium animalis*, *Bifidobacterium lactis*, *Bifidobacterium infantis*, *Bifidobacterium adolescentis* and *Bifidobacterium pseudocatenulatum*, and mixtures thereof.

The species that are most particularly suitable for use are *Lactobacillus johnsonii*, *Lactobacillus paracasei*, *Bifidobacterium adolescentis*, *Bifidobacterium longum* and *Bifidobacterium lactis* NCC 2818 (also known as Bb12 ATCC 27536), which were deposited, respectively, according to the treaty of Budapest, at the Institut Pasteur (28, rue du Docteur Roux, F-75024 Paris cedex 15) on Jun. 30, 1992, Jan. 12, 1999, Apr. 15, 1999 and Jun. 7, 2005 under the following designations CNCM I-1225, CNCM I-2116, CNCM I-2168 and CNCM I-2170 and CNCM I-3446, and the genus *Bifidobacterium longum* (BB536). The strain of *Bifidobacterium lactis* CNCM I-3446 may be obtained from Hansen (Chr. Hansen A/S, 10-12 Boege Alle, P.O. Box 407, DK-2970 Hoersholm, Denmark).

According to one particular embodiment of the invention, the composition comprises at least two different microorganisms, which are especially probiotic, and/or metabolites and/or fractions thereof. These microorganisms may differ by their nature, for example bacterium and fungus, or alternatively by their family, their genus or their species, or only by their strain.

The prebiotic agents that are suitable for use in the invention may be chosen from oligosaccharides, produced from glucose, galactose, xylose, maltose, sucrose, lactose, starch, xylan, hemicellulose, inulin, gums of acacia type, for example, or a mixture thereof. More particularly, the oligosaccharide comprises at least one fructo-oligosaccharide.

More particularly, this prebiotic may comprise a mixture of fructo-oligosaccharide and of inulin.

Composition and Kits

According to one aspect of the invention, a combination of active agents in accordance with the invention may be used in a cosmetic or nutritional composition that is suitable for oral administration.

A composition in accordance with the invention comprises a physiologically or pharmaceutically acceptable medium.

Needless to say, a person skilled in the art will take care to select the additional active agents and the amount thereof such that the advantageous properties of the composition in accordance with the invention are not, or are not substantially, adversely affected by the envisaged addition.

A combination of active agents and a composition in accordance with the invention make it possible, via their oral administration, to improve, reinforce or restore an aesthetic state of a nail.

As indicated previously, various intrinsic or extrinsic factors may be the cause of an esthetically degraded state of the nails. The object of the present invention is to restore this state without treating or preventing the cause thereof, and is thus limited to the cosmetic field. The invention does not relate to the therapeutic field.

According to one embodiment, the invention is directed towards reducing and/or preventing an impairment in the structure of the nails, in particular to reduce and/or prevent brittle, fragile, soft, split or cracked nails, preferably split nails.

For the purposes of the invention, the expression "impairment in the structure of the nails" means an impairment in the organization of the keratin fibres or of their chemical composition constituting the nails with regard to an organization or a composition observed in nails of healthy aesthetic quality.

More particularly, the impairments in the structure of the nails may lead to the presence of striations on the surface of the nails. Thus, the invention is also directed towards reducing and/or preventing striated nails.

According to one embodiment, the combination of active agents under consideration in the invention promotes and/or improves the flexibility and/or hardness of the nails. Following the use of the combination of active agents in accordance with the invention, the nails are found to be less brittle, harder, more flexible, and/or more resistant to impacts, and have less of a tendency to split.

According to one embodiment, the combination of active agents in accordance with the invention also makes it possible to make the nails sleek, shiny and/or translucent.

In particular, the combination of active agents in accordance with the invention makes it possible to increase the transparency and/or sheen of the nails, as indicated in the tests presented hereinbelow.

According to one embodiment, the combination of active agents in accordance with the invention also makes it possible to improve the general aesthetic appearance of the nails.

According to the present invention, it is considered that the general aesthetic appearance of a nail is improved when at least one of the parameters chosen from the hardness, the solidity, the resistance to impacts or to external attacking factors, the resistance to splitting, the sleek appearance and/or the sheen is improved.

The combination of active agents in accordance with the invention or the composition in accordance with the invention is administered orally.

The combinations and compositions in accordance with the invention, intended for oral administration, may especially comprise all or only part of the daily dose.

The required daily dose may thus be fractionated so as to be taken, for example, 1 to 3 times in the day.

Typically, the duration of this cosmetic treatment may be longer than 4 weeks, especially from 4 to 15 weeks, with, where appropriate, one or more periods of stoppage.

The oral route has the advantage of acting in a more overall manner on the whole of the structure of the nails.

The expression "oral cosmetic composition" means, for example, nutritional, nutraceutical or cosmeceutical compositions, comprising at least a combination of active agents in accordance with the invention.

In the case of compositions that are suitable for oral administration, the use of an ingestible support is preferred. The ingestible support may be of diverse nature according to the type of composition under consideration.

For ingestion, numerous embodiments of oral compositions and especially of food supplements are possible.

Such compositions may be formulated via any common process known to those skilled in the art.

Thus, a composition in accordance with the invention may preferably take the form of a coated tablet, a gel capsule, a suspension, a gel, an emulsion, a drinkable solution, a tablet to be swallowed or chewed, a capsule, especially a soft or hard capsule, a granule to be dissolved, a syrup, a lozenge or a food supplement.

It may preferably be in the form of a soft or hard capsule, preferably a soft capsule.

In particular, a combination of active agents in accordance with the invention may be incorporated into any form of food supplement or enriched food, for example food bars or compacted or loose powders. The powders may be diluted with water, in soda, dairy products or soybean derivatives, or may be incorporated into food bars.

According to one preferred embodiment, a composition in accordance with the invention administered orally may be formulated in the form of coated tablets, gel capsules, gels, emulsions, tablets, capsules, hydrogels, food bars, compacted or loose powders, liquid suspensions or solutions, confectionery products, fermented milks, fermented cheeses, chewing gum, toothpaste or spray solutions.

Milk, yoghurt, cheese, fermented milks, milk-based fermented products, ice creams, fermented or nonfermented cereal-based products, milk-based powders, infant and baby formulae, animal feed in particular for pets, tablets or lozenges, liquid bacterial suspensions, oral supplements in dry form and oral supplements in liquid form are, for example, suitable as food supplements.

The oral compositions may be either in anhydrous form or in aqueous form.

A combination of active agents in accordance with the invention may be formulated with the usual excipients and components for such oral compositions or food supplements, i.e. especially fatty and/or aqueous components, humectants, thickeners, preserving agents, texture agents, taste agents and/or coating agents, antioxidants, preserving agents and dyes that are common in the food sector.

The formulating agents and excipients for oral compositions, and especially for food supplements, are known in this field and are not the subject of a detailed description herein.

In particular, a composition in accordance with the invention may be a food composition for human consumption. This may be, in particular, nutritional complete foods, drinks, mineral waters, soups, dietary supplements and replacement or substitute foods, nutritional bars, confectionery, milk-based products or fermented milk-based products, yoghurts, milk-based powders, enteral nutritional products, infant and/or baby compositions, fermented or nonfermented cereal-based products, ice creams, chocolate, coffee, "culinary" products such as mayonnaise, tomato puree or salad dressings.

The present invention also relates to a packaging kit or assembly comprising:

(i) a combination of active agents in accordance with the invention intended for oral administration, and (ii) an antifungal agent intended for topical application, the combination of active agents and the antifungal agent (i) and (ii) being intended to be administered independently of each other, separately, simultaneously or consecutively over time, the antifungal agent (ii) advantageously being administered before the combination of active agents (i).

According to yet another of its aspects, the present invention relates to a packaging kit or assembly comprising:

(i) a combination of active agents in accordance with the invention intended for oral administration, and (ii) a moisturizer and/or a hardener intended for topical application, the combination of active agents (i) and the moisturizer and/or hardener (ii) being intended to be administered independently of each other, separately, simultaneously or consecutively over time.

According to one embodiment, a kit according to the invention uses an antifungal agent. Such an agent may be chosen from the family of imidazoles, morpholines or pyridones.

According to another embodiment, a kit according to the invention uses a moisturizer and/or a hardener.

A moisturizer in accordance with the invention may be chosen from vitamins and oils. As examples of oils that are suitable for use as moisturizers, mention may be made especially of argan oil, sesame seed oil and sunflower oil.

A hardener in accordance with the invention may be chosen from hydrolysed wheat proteins, calcium pantothenate or vitamin B5, iron, epoxy resins and polyesters, and nitrocellulose.

Process

According to another of its aspects, the present invention relates to a cosmetic process for improving the quality of the nails, in an individual in need thereof, characterized in that it comprises at least the oral administration, to the said individual, of a combination of active agents or of a composition in accordance with the invention.

A process according to the invention may comprise a step that consists in observing a reduction in, or even disappearance of, the impairment in the quality of the nails.

Advantageously, the application of a process of the invention gives the advantages indicated previously as being combined with the use of a combination of active agents or of a composition in accordance with the invention, and may especially improve, or even restore, the hardness, the resistance to impacts, a physiological form, a sleek appearance and a translucent appearance.

A cosmetic process according to the invention may be performed especially by administering a food composition as defined above.

A process of the invention may be performed on a daily basis, for example, for instance at a rate of one administration per day or one administration twice a day, for example once in the morning and once in the evening, or three times a day, in particular with each meal.

A cosmetic process according to the invention may be performed, for example, by daily administration of a composition formulated, for example, in the form of gel capsules, coated tablets, emulsions, tablets, capsules or oral vials, in appropriate amount and number, depending on their form.

An effective amount of a combination of active agents in accordance with the invention may be administered in a single dose per day or in fractional doses over the day, for example two to three times a day.

A process according to the invention may advantageously comprise a single administration.

A cosmetic process may be performed over a time period ranging from one week to several weeks, or even several months, this period moreover possibly being repeated after periods without treatment, for several months or even several years.

By way of example, the administration of a combination of active agents in accordance with the invention may be performed at a rate, for example, of three times a day, generally over a prolonged period of at least 4 weeks, or even 4 to 15 weeks, optionally comprising one or more periods of stoppage or being repeated after a period of stoppage.

In the description and the examples that follow, unless otherwise mentioned, the percentages are weight percentages and the ranges of values written in the form "between . . . and . . . " include the stated lower and upper limits. The ingredients are mixed, before being formed, in the order and under conditions that are easily determined by those skilled in the art.

The example below is given as a non-limiting illustration of the field of the invention.

EXAMPLES

Example 1

Oral Composition in the Form of a Soft Capsule

| Ingredients | Suppliers | Trade name | (mg/soft capsule) | (% by weight relative to the total weight of the composition) |
|---|---|---|---|---|
| Fish oil (1) | Polaris | Omegavie 1812 TG | 230.0 | 31.1 |
| blackcurrant seed oil (2) | Bioriginal | Blackcurrant Oil Refined | 230.0 | 31.1 |
| Vitamin E (3) | BASF/DSM | Vitamin E acetate/ D,L-α- tocopheryl acetate | 4.2 | 0.5 |
| Vitamin C (4) | DSM | Ascorbic acid fine powder | 21.0 | 2.8 |
| Tomato extract (5) | Lycored | Lyc-O-Mato 10% | 5.5 | 0.7 |

-continued

| Ingredients | Suppliers | Trade name | (mg/soft capsule) | (% by weight relative to the total weight of the composition) |
|---|---|---|---|---|
| Excipients | | | | |
| Glyceryl monostearate | Gattefosse | Geleol | 32.5 | 4.3 |
| Soybean lecithin | Sternchemie | Yellothin 100 IP | 5.7 | 0.7 |
| Capsule | | | | |
| Fish gelatin | Weishardt | Gelatine 200 Bloom Grain - Fish | 144.6 | 19.5 |
| Glycerol | Peter Cremer | Refined Glycerine 99.5% | 58.6 | 7.9 |
| Purified water | SCA | Purified Water | 6.8 | 0.9 |

(1): Omegavie 1812TG: Calculation of the fatty acid distribution amount of EPA (5,8,11,14,17-eicosapentaenoic acid) (omega 3): 34.5 mg/soft capsule amount of DHA (4,7,10,13,16,19-docosahexaenoic acid) (omega 3): 20.7 mg/soft capsule
(2): Blackcurrant Oil Refined: Calculation of the fatty acid distribution amount of LA (linolenic acid) (omega 6): 80.73 mg/soft capsule amount of GLA (γ-linolenic acid) (omega 6): 26.91 mg/soft capsule amount of ALA (α-linolenic acid) (omega 3): 22.77 mg/soft capsule amount of SDA (stearidonic acid) (omega 3): 5.06 mg/soft capsule
(3): Vitamin E contribution: 2.5 mg/soft capsule
(4): Vitamin C contribution: 15 mg/soft capsule
(5): Lycopene contribution: 0.5 mg/soft capsule One to four of these soft capsules may be taken per day.

This composition was prepared according to the process illustrated below:

A soft capsule according to the invention may be prepared in the following manner.

The fish oil, the blackcurrant seed oil, the vitamin E, the tomato extract and the additives are mixed together in the presence of nitrogen. The mixture is then homogenized and encapsulated in a soft capsule consisting of fish gelatin, glycerol and purified water.

Example 2

A single-blind study was performed, on the basis of the composition of Example 1, under dermatological control, on 50 healthy women from 18 to 50 years old, having fragile/split nails.

These women were supplemented for 3 months with the composition of Example 1. The efficacy of the supplementation was then validated by clinical scoring and self-evaluation.

The results obtained are presented in the tables below.

1. Onychoschizia Clinical Scores

TABLE 1

| | Mean | | | |
|---|---|---|---|---|
| | T0 | T1 month | T2 months | T3 months |
| Lamellar separation (1) | 1.4 | 1.1 | 0.8 | 1.1 |
| Transverse separation (2) | 0.1 | 0.1 | 0.1 | 0.1 |
| Onychoschizia score (1 + 2) | 1.5 | 1.2 | 0.9 | 1.2 |

The onychoschizia score decreases in a statistically significant manner from 1 month of supplementation with the combination according to the invention, demonstrating the efficacy of the formulation on splitting of the nails.

2. Overall Clinical Efficacy Score

The overall clinical efficacy score measures the change between time T0 and T1 month, T0 and T2 months and T0 and T3 months of the embrittled nature of the nail.

This score is evaluated by means of a 5-point scale as indicated in the table below. The results are presented in terms of number and frequency.

TABLE 2

| | T1 month | T2 months | T3 months |
|---|---|---|---|
| 0 Deterioration | 8% | 0% | 4% |
| 1 No improvement | 56% | 34% | 34% |
| 2 Moderate | 22% | 42% | 26% |
| 3 Good | 10% | 14% | 30% |
| 4 Excellent | 4% | 10% | 6% |

From 1 month of supplementation with the combination in accordance with the invention, the clinician notes a marked improvement in the embrittled nature of the nail for 32% of the individuals.

The improvement concerns 66% and 62% of the women after, respectively, 2 and 3 months of supplementation.

3. Self-Evaluation of the Quality of the Nails by the Individuals of the Study

TABLE 3

| Population | | T1 month % | T2 months % | T3 months % |
|---|---|---|---|---|
| With the supplementation, my nails split less | Entirely in agreement | 8 | 32 | 38 |
| | Quite in agreement | 38 | 52 | 44 |

TABLE 3-continued

| Population | | T1 month % | T2 months % | T3 months % |
|---|---|---|---|---|
| | Remotely in agreement | 32 | 14 | 18 |
| | Not at all in agreement | 20 | 2 | 0 |
| | No opinion | 2 | 0 | 0 |
| With the supplementation, my nails crack less | Entirely in agreement | 8 | 46 | 40 |
| | Quite in agreement | 36 | 20 | 40 |
| | Remotely in agreement | 42 | 2 | 14 |
| | Not at all in agreement | 10 | 2 | 6 |
| | No opinion | 4 | 4.1 | 0 |
| With the supplementation, my nails appear to be less damaged | Entirely in agreement | 10 | 20 | 40 |
| | Quite in agreement | 40 | 60 | 52 |
| | Remotely in agreement | 36 | 18 | 8 |
| | Not at all in agreement | 14 | 2 | 0 |
| | No opinion | 0 | 0 | 0 |
| With the supplementation, my nails are less brittle | Entirely in agreement | 8 | 28 | 32 |
| | Quite in agreement | 26 | 42 | 40 |
| | Remotely in agreement | 40 | 22 | 22 |
| | Not at all in agreement | 26 | 8 | 6 |
| | No opinion | 0 | 0 | 0 |
| With the supplementation, my nails are less striated | Entirely in agreement | 6 | 8 | 26 |
| | Quite in agreement | 40 | 44 | 38 |
| | Remotely in agreement | 32 | 32 | 24 |
| | Not at all in agreement | 14 | 8 | 6 |
| | No opinion | 8 | 8 | 6 |
| With the supplementation, my nails are more solid | Entirely in agreement | 8 | 18 | 32 |
| | Quite in agreement | 26 | 56 | 46 |
| | Remotely in agreement | 46 | 22 | 20 |
| | Not at all in agreement | 20 | 4 | 2 |
| | No opinion | 0 | 0 | 0 |
| The food supplement makes my nails shinier | Entirely in agreement | 6 | 10 | 8 |
| | Quite in agreement | 24 | 44 | 50 |
| | Remotely in agreement | 44 | 32 | 32 |
| | Not at all in agreement | 20 | 8 | 2 |
| | No opinion | 6 | 6 | 8 |
| The food supplement makes my nails more beautiful | Entirely in agreement | 4 | 18 | 18 |
| | Quite in agreement | 28 | 50 | 66 |
| | Remotely in agreement | 48 | 30 | 16 |
| | Not at all in agreement | 14 | 0 | 0 |
| | No opinion | 6 | 2 | 0 |

The majority of the women participating in the study noted the efficacy of the combination in accordance with the invention.

The invention claimed is:

1. Oral cosmetic method comprising at least the oral administration of a combination of active agents comprising at least one polyunsaturated fatty acid and at least one carotenoid, for improving the quality of the nails, wherein:
   the at least one polyunsaturated fatty acid is used in the form of a blackcurrant seed oil and a fish oil, and the carotenoid used is lycopene, and
   wherein the combination also comprises, as additional active agents, vitamin C and vitamin E, and
   wherein the improvement of the quality of nails comprises reducing and/or preventing brittle, fragile, split, or cracked nails.

2. Method according to claim 1, wherein the polyunsaturated fatty acid and the carotenoid, are used in a polyunsaturated fatty acid/carotenoid ratio of between 55/6 and 500/0.5.

3. Method according to claim 1, wherein the combination also comprises at least one arterial pressure modulator selected from the group consisting of vitamin D, taurine, cysteine, arginine, citrulline, glutamate, tryptophan, leucine, a tripeptide selected from the group consisting of Val-Pro-Pro and isoleucine-proline-proline, adenosine, flavonoids from berries, onions, pomegranate, red wine, grapes including the seeds, tea, cocoa and dark chocolate, coenzyme Q10, acetyl-L-carnitine, α-lipoic acid, soybean proteins, spirulina; a microorganism selected from the group consisting of Lactobacillus helveticus, Bifidobacterium longum, Lactobacillus acidophilus, L. casei, L. acidophilus, Saccharomyces cerevisiae, Streptococcus thermophilus; prebiotic agents, glutathione, soybean isoflavones, soybean lecithin and a tomato extract, and mixtures thereof.

4. Method according to claim 1, in which the combination of active agents is used in a cosmetic composition that is suitable for oral administration, the said composition being in the form of a coated tablet, a gel capsule, a suspension, a gel, an emulsion, a drinkable solution, a tablet to be swallowed or chewed, a capsule, a granule to be dissolved, a syrup, a lozenge or a food supplement.

5. Method according to claim 4, in which the said at least one polyunsaturated fatty acid is present in a content ranging from 1% to 80% by weight, relative to the total weight of the composition.

6. Method according to claim 4, wherein the carotenoid is present in a content ranging from 0.01% to 6% by weight, relative to the total weight of the composition.

7. Method according to claim 1, in which the carotenoid used is lycopene in the form of a lycopene-rich tomato extract.

8. Method according to claim 1 for increasing the transparency and/or whiteness and/or sheen of the nails.

9. Method according to claim 2, wherein the polyunsaturated fatty acid/carotenoid ratio is between 19/1 and 300/0.5.

10. Method according to claim 5, in which the said at least one polyunsaturated fatty acid is present in a content ranging from 20% to 40% by weight relative to the total weight of the composition.

11. Method according to claim 6, wherein the carotenoid is present in a content ranging from 0.05% to 2% by weight relative to the total weight of the composition.

* * * * *